United States Patent
Zhang et al.

(10) Patent No.: US 10,039,499 B2
(45) Date of Patent: Aug. 7, 2018

(54) DETECTING HEART FAILURE BY MONITORING THE TIME SEQUENCE OF PHYSIOLOGICAL CHANGES

(71) Applicant: Cardiac Pacemakers, Inc., St. Paul, MN (US)

(72) Inventors: Yi Zhang, Plymouth, MN (US); Viktoria A. Averina, Shoreview, MN (US); Abhilash Patangay, Inver Grove Heights, MN (US); Ramesh Wariar, Blaine, MN (US); Jon Peterson, Mahtomedi, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 62 days.

(21) Appl. No.: 15/216,167

(22) Filed: Jul. 21, 2016

(65) Prior Publication Data
US 2016/0324480 A1 Nov. 10, 2016

Related U.S. Application Data

(63) Continuation of application No. 13/324,142, filed on Dec. 13, 2011, now Pat. No. 9,420,959.
(Continued)

(51) Int. Cl.
*A61B 5/00* (2006.01)
*A61B 5/0402* (2006.01)
(Continued)

(52) U.S. Cl.
CPC ............ *A61B 5/7264* (2013.01); *A61B 5/002* (2013.01); *A61B 5/0031* (2013.01);
(Continued)

(58) Field of Classification Search
None
See application file for complete search history.

(56) References Cited

U.S. PATENT DOCUMENTS

| 6,275,727 B1 | 8/2001 | Hopper et al. |
| 6,752,765 B1 | 6/2004 | Jensen et al. |

(Continued)

FOREIGN PATENT DOCUMENTS

| EP | 1133256 B1 | 7/2005 |
| EP | 0898460 B1 | 8/2006 |

(Continued)

OTHER PUBLICATIONS

"U.S. Appl. No. 13/324,142, Advisory Action dated Aug. 18, 2015", 3 pgs.
(Continued)

*Primary Examiner* — Erica Lee
(74) *Attorney, Agent, or Firm* — Schwegman Lundberg & Woessner, P.A.

(57) ABSTRACT

Systems and methods for detecting heart failure by monitoring the time-sequence of physiological changes of a subject using a state machine circuit configured to receive information about physiological characteristics of the subject is described. The current state transitions between a first and a second state in response to a first transition trigger. The current state transitions between the second and first states in response to at least one of the expiration of a first timer or ceasing of the first transition trigger. The current state transitions between the second and third states in response to a second transition trigger. The current state transitions between the third and second states in response to at least one of expiration of a second timer or ceasing of the second transition trigger.

18 Claims, 8 Drawing Sheets

Related U.S. Application Data

(60) Provisional application No. 61/423,126, filed on Dec. 15, 2010.

(51) Int. Cl.

| | | |
|---|---|---|
| *A61B 5/042* | (2006.01) | |
| *A61B 5/08* | (2006.01) | |
| *A61B 7/00* | (2006.01) | |
| *A61B 7/04* | (2006.01) | |
| *A61B 5/053* | (2006.01) | |

(52) U.S. Cl.
CPC ............ *A61B 5/0402* (2013.01); *A61B 5/042* (2013.01); *A61B 5/0816* (2013.01); *A61B 5/4842* (2013.01); *A61B 5/686* (2013.01); *A61B 5/7282* (2013.01); *A61B 5/746* (2013.01); *A61B 7/00* (2013.01); *A61B 7/04* (2013.01); *A61B 5/0538* (2013.01); *A61B 2562/06* (2013.01)

(56) References Cited

U.S. PATENT DOCUMENTS

| | | |
|---|---|---|
| 6,811,537 B2 | 11/2004 | Bardy |
| 7,115,096 B2 | 10/2006 | Siejko et al. |
| 7,127,290 B2 | 10/2006 | Girouard et al. |
| 7,299,086 B2 | 11/2007 | McCabe et al. |
| 7,558,623 B2 | 7/2009 | Fischell et al. |
| 7,629,889 B2 | 12/2009 | Sachanandani et al. |
| 7,761,158 B2 | 7/2010 | Brockway et al. |
| 7,764,996 B2 | 7/2010 | Zhang et al. |
| 9,420,959 B2 | 8/2016 | Zhang et al. |
| 2006/0047538 A1* | 3/2006 | Condurso ............ G06F 19/326 705/3 |
| 2006/0247548 A1 | 11/2006 | Sarkar et al. |
| 2007/0265510 A1 | 11/2007 | Bardy |
| 2007/0299356 A1 | 12/2007 | Wariar et al. |
| 2008/0064968 A1* | 3/2008 | Martin ................. A61B 5/0048 600/493 |
| 2009/0069708 A1 | 3/2009 | Hatlestad et al. |
| 2009/0143663 A1 | 6/2009 | Chetham |
| 2009/0287106 A1 | 11/2009 | Zhang et al. |
| 2010/0030293 A1 | 2/2010 | Sarkar et al. |
| 2010/0045467 A1 | 2/2010 | Jon et al. |
| 2010/0114206 A1 | 5/2010 | Kaemmerer et al. |
| 2010/0145407 A1 | 6/2010 | Vanderlinde et al. |
| 2010/0198097 A1 | 8/2010 | Sowelam |
| 2011/0009753 A1 | 1/2011 | Zhang et al. |
| 2011/0015704 A1 | 1/2011 | Ternes et al. |
| 2011/0264164 A1* | 10/2011 | Christopherson .... A61B 5/0803 607/42 |
| 2012/0157797 A1 | 6/2012 | Zhang et al. |

FOREIGN PATENT DOCUMENTS

| | | |
|---|---|---|
| EP | 1151719 B1 | 9/2007 |
| EP | 1635704 B1 | 5/2009 |
| EP | 1339451 B1 | 9/2009 |
| EP | 2147693 A1 | 1/2010 |
| WO | WO-2010024738 A1 | 3/2010 |
| WO | WO-2010042790 A2 | 4/2010 |

OTHER PUBLICATIONS

"U.S. Appl. No. 13/324,142, Final Office Action dated Jun. 4, 2015", 12 pgs.

"U.S. Appl. No. 13/324,142, Non Final Office Action dated Oct. 2, 2015", 15 pgs.

"U.S. Appl. No. 13/324,142, Non Final Office Action dated Dec. 16, 2014", 11 pgs.

"U.S. Appl. No. 13/324,142, Notice of Allowance dated Apr. 21, 2016", 12 pgs.

"U.S. Appl. No. 13/324,142, Response filed Feb. 9, 2015 to Non Final Office Action dated Dec. 16, 2014", 9 pgs.

"U.S. Appl. No. 13/324,142, Response filed Jul. 14, 2015 to Final Office Action dated Jun. 4, 2015", 10 pgs.

"U.S. Appl. No. 13/324,142, Response filed Aug. 27, 2014 to Restriction Requirement dated Jul. 10, 2014", 8 pgs.

"U.S. Appl. No. 13/324,142, Response filed Sep. 4, 2015 to Advisory Action dated Aug. 18, 2015", 10 pgs.

"U.S. Appl. No. 13/324,142, Response filed Dec. 31, 2015 to Non Final Office Action dated Oct. 2, 2015", 12 pgs.

"U.S. Appl. No. 13/324,142, Restriction Requirement dated Jul. 10, 2014", 7 pgs.

"U.S. Appl. No. 12/787,777, Respiration Rate Trending for Detecting Early Onset of Worsening Heart Failure, filed May 26, 2010", 68 pgs.

* cited by examiner ns"2"># DETECTING HEART FAILURE BY MONITORING THE TIME SEQUENCE OF PHYSIOLOGICAL CHANGES

CLAIM OF PRIORITY

This application is a continuation of U.S. application Ser. No. 13/324,142, filed Dec. 13, 2011, which claims the benefit of priority under 35 U.S.C. § 119(e) of Zhang et al., U.S. Provisional Patent Application Ser. No. 61/423,126, entitled "DETECTING HEART FAILURE BY MONITORING THE TIME SEQUENCE OF PHYSIOLOGICAL CHANGES", filed on Dec. 15, 2010, each of which is herein incorporated by reference in its entirety.

BACKGROUND

Heart failure, also known as congestive heart failure, is a leading cause of cardiovascular disease-related death. Heart failure is an abnormality of cardiac function in which cardiac output is not able to meet the needs of peripheral tissue. The early detection of heart failure is often difficult because of the many underlying causes, such as ischemic heart disease (coronary artery disease), hypertension (high blood pressure), and diabetes. Because the causes of heart failure are varied, the onset can be subtle (e.g., without overt symptoms) and difficult for a patient to recognize. As a result, the patient may alter his or her daily activities rather than making an appointment to be evaluated by his physician. When symptoms are missed, the patient faces an increased risk of an acute decompensated heart-failure event that requires hospitalization.

An implantable or other ambulatory medical device can be used to monitor a physiological condition of a patient, such as a patient at risk for a worsening heart failure condition. For example, a cardiac function management device, such as an implantable pacemaker, cardioverter-defibrillator, or a cardiac resynchronization device can be implanted into or otherwise provided to a patient. The cardiac function management device can be used treat the patient's cardiac condition. For example, it can be configured to deliver electrical stimulation or other therapy. Such devices can be used for internal or other ambulatory monitoring of the patient's condition such as to aid in diagnosis. The devices can include or be coupled to one or more electrodes, such as in communication with one or more sense amplifiers, such as to monitor electrical heart activity within a patient. Such devices can include one or more sensors, such as to monitor one or more patient physiological parameters. Other examples of medical devices can include implantable diagnostic devices, implantable drug delivery systems, or implantable devices with neural stimulation capability.

An example of a system and method for diagnosing and monitoring of congestive heart failure for use in automated patient care by comparing recorded physiological measures to at least one other recorded physiological measure to quantify a change in patient status is described in U.S. Pat. No. 6,811,537 to Bardy, entitled, "System and Method for Providing Diagnosis and Monitoring of Congestive Heart Failure for use in Automated Patient Care."

An example of detecting myocardial ischemia by monitoring a time-wise sequential cascade of physiologic cardiovascular events corresponding to electrical sensor signals is described in U.S. patent application Ser. No. 11/426,835 to Wariar, et al., entitled, "Detection of Myocardial Ischemia from the Time Sequence of Implanted Sensor Measurements."

OVERVIEW

The present inventors have recognized, among other things, that better evaluation of physiological sensor information can allow early detection and intervention. This can help inhibit or prevent serious heart failure decompensation, which can involve hospitalization. Patients that are hospitalized for decompensated heart failure are readmitted with high frequency. Monitoring the time course of a patient's recovery could be used to ensure that the patient receives early intervention during the vulnerable post-hospitalization period. This document describes, among other things, techniques that can permit early evaluation of disease symptoms, which can increase opportunities for effective treatment or offer various other advantages.

Example 1 can include subject matter (such as a system, a method, a means for performing acts, or a machine-readable medium including instructions that, when performed by the machine, cause the machine to perform acts, etc.) that can include a state machine circuit, configured to receive information about different first and second physiological characteristics. The state machine can include: (1) a state sequence of at least first, second, and third states; (2) a first forward state transition between the first and second states in response to a first transition trigger; (3) a first reverse state transition between the second and first states in response to at least one of expiration of a first timer or ceasing of the first transition trigger; (4) a second forward state transition between the second and third states in response to a second transition trigger; and (5) a second reverse state transition between the third and second states in response to at least one of expiration of a second timer or ceasing of the second transition trigger, wherein the second timer is capable of being set to a different time limit value from the first timer.

In Example 2, the subject matter of Example 1 can optionally be configured such that the first reverse state transition is in response to the expiration of a third timer, wherein the third timer corresponds with a maximum time to complete the state sequence.

In Example 3, the subject matter of one or any combination of Examples 1-2 can optionally include a third reverse state transition, wherein the third reverse state transition is in response to the expiration of the third timer.

In Example 4, the subject matter of one or any combination of Examples 1-3 can optionally include a plurality of physiological sensors, wherein the physiological sensors produce respective physiological signals including information about the first and second physiological characteristics.

In Example 5, the subject matter of one or any combination of Examples 1-4 can optionally be configured such that the plurality of physiologic sensors includes at least one ambulatory sensor.

In Example 6, the subject matter of one or any combination of Examples 1-5 can optionally be configured such that the first and second transition triggers further include a time sequence parameter, wherein the time sequence parameter corresponds to a minimum time prior to triggering the first and second forward state transition.

In Example 7, the subject matter of one or any combination of Examples 1-6 can optionally be configured such that the first state comprises a baseline condition of a subject, wherein the baseline condition is associated with the first and second physiological characteristics.

In Example 8, the subject matter of one or any combination of Examples 1-7 can optionally include a response circuit coupled to the state machine circuit, wherein the response circuit is operable to provide a specified response following the second forward state transition to the third state.

In Example 9, the subject matter of one or any combination of Examples 1-8 can optionally be configured such that the specified response includes an alert.

In Example 10, the subject matter of one or any combination of Examples 1-9 can optionally be configured such that the specified response includes a report.

In Example 11, the subject matter of one or any combination of Examples 1-10 can optionally be configured such that the third state corresponds to a clinical event of a subject.

In Example 12, the subject matter of one or any combination of Examples 1-11 can optionally be configured such that the third state further corresponds to a worsening heart failure event of the subject.

In Example 13, the subject matter of one or any combination of Examples 1-12 can optionally be configured such that the first and second timers are capable of being set with a variable time limit value, wherein the variable time limit value corresponds with at least one of the first and second physiological characteristics.

In Example 14, the subject matter of one or any combination of Examples 1-13 can optionally be configured such that the state machine circuit further comprises: (1) the state sequence, wherein the state sequence further comprises a fourth state; (2) a third forward state transition between the first and fourth states in response to a third transition trigger; (3) a fourth reverse state transition between the fourth and first states in response to at least one of expiration of a fourth timer or ceasing of the third transition trigger, wherein the fourth timer is capable of being set to a different time limit value than the first, second and third timer values; (4) a fourth forward state transition between the fourth and second states in response to a fourth transition trigger; and (5) a fifth reverse state transition between the second and fourth states in response to at least one of expiration of a fifth timer or ceasing of the third transition trigger, wherein the fifth timer is capable of being set to a different time limit value than the first, second, third and fourth timer values.

Example 15 can include, or can be combined with the subject matter of one or any combination of Examples 1-14 to optionally include, subject matter (such as an apparatus, a method, a means for performing acts, or a machine-readable medium including instructions that, when performed by the machine, cause the machine to perform acts) that can comprise: receiving information about different first and second physiological characteristics of a subject, transitioning from a first state to a second state in response to a first transition trigger; transitioning from the second state to the first state in response to at least one of expiration of a first timer or ceasing of the first transition trigger; transitioning from the second state to a third state in response to a second transition trigger; and transitioning from the third state to the second state in response to at least one of expiration of a second timer or ceasing of the second transition trigger.

In Example 16, the subject matter of one or any combination of Examples 1-15 can optionally include receiving a plurality of physiological signals from respective physiological sensors, wherein the physiological signals include information about the first and second physiological characteristics.

In Example 17, the subject matter of one or any combination of Examples 1-16 can optionally be configured such that the physiological sensors include at least one ambulatory sensor.

In Example 18, the subject matter of one or any combination of Examples 1-17 can optionally be configured such that transitioning from the second state to the first state further includes a response to the expiration of a third timer, wherein the third timer corresponds with a maximum time to complete the state sequence.

In Example 19, the subject matter of one or any combination of Examples 1-18 can optionally include transitioning from the third state to the first state in response to the expiration of the third timer.

In Example 20, the subject matter of one or any combination of Examples 1-19 can optionally be configured such that the first and second transition triggers further include a time sequence parameter, wherein the time sequence parameter corresponds to a minimum time prior to transitioning from the first state to the second state or transitioning from the second state to the third state.

In Example 21, the subject matter of one or any combination of Examples 1-20 can optionally be configured such that the first state comprises a baseline condition of a subject, wherein the baseline condition is associated with the first and second physiological characteristics.

In Example 22, the subject matter of one or any combination of Examples 1-21 can optionally include communicating a specified response after transitioning from the second state to the third state.

In Example 23, the subject matter of one or any combination of Examples 1-22 can optionally be configured such that the specified response includes an alert.

In Example 24, the subject matter of one or any combination of Examples 1-23 can optionally be configured such that the specified response includes a report.

In Example 25, the subject matter of one or any combination of Examples 1-24 can optionally be configured such that the third state corresponds to a clinical event of a subject.

In Example 26, the subject matter of one or any combination of Examples 1-25 can optionally be configured such that the third state further corresponds to a worsening heart failure event of the subject.

In Example 27, the subject matter of one or any combination of Examples 1-26 can optionally include setting the first and second timers with a variable time limit value, wherein the variable time limit value corresponds with at least one of the first and second physiological characteristics.

In Example 28, the subject matter of one or any combination of Examples 1-27 can optionally include transitioning between the first state and a fourth state in response to a third transition trigger; transitioning between the fourth and first states in response to at least one of expiration of a fourth timer or ceasing of the third transition trigger, wherein the fourth timer is capable of being set to a different time limit value than the first, second and third timer values; transitioning between the fourth and second states in response to a fourth transition trigger; and transitioning between the second and fourth states in response to at least one of expiration of a fifth timer or ceasing of the third transition trigger, wherein the fifth timer is capable of being set to a different time limit value than the first, second, third and fourth timer values.

These examples can be combined in any permutation or combination. This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals can describe similar components in different views. Like numerals having different letter suffixes can represent different instances of similar components. The drawings illustrate generally, by way of example, but not by way of limitation, various examples discussed in the present document.

DETAILED DESCRIPTION

This document discusses improved systems and methods to predict or detect changes to heart failure status, such as monitoring the development of or the recovery from worsening heart failure conditions. For example, systems and methods to predict or detect worsening heart failure, such as monitoring the time-sequence of changes to one or more physiological signals associated with a subject, are described.

Figure 1:
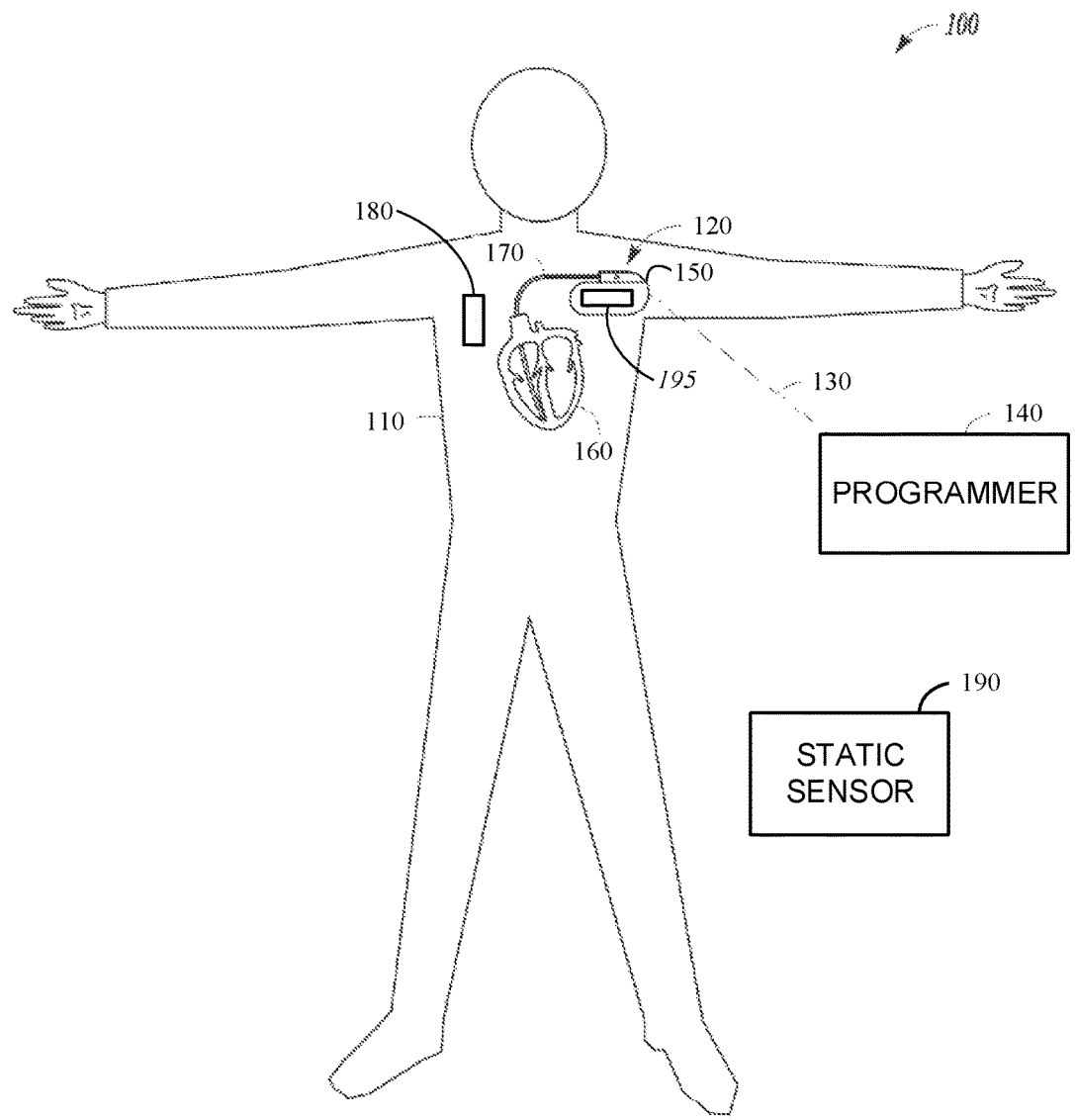
FIG. 1 is an example of a block diagram of portions of an example of a system that can include or use an implantable medical device (IMD) or other ambulatory medical device.

FIG. 1 is an example of a block diagram of portions of an example of a system 100 such as to monitor one or more physiological changes such as to detect worsening heart failure of a subject 110. Often, the subject 110 at risk for a worsening heart failure condition can suffer from other health issues, such as cardiac arrhythmia, hypertension, chronic obstructive pulmonary disease, or renal disease. In FIG. 1, the system 100 can include an ambulatory system, such as the implantable system 120, which can communicate, such as using a telemetry link 130, to an external monitoring system 140. In an example, the external monitoring system 140 can include a programming device. In an example, the external monitoring system 140 can include a local monitoring device, which can be capable of communicating with a remote monitoring device, such as can be located in a physician's office.

The implantable system 120 can include an ambulatory device, such as IMD 150, which can be coupled to a heart 160, such as using a cardiac lead 170. Examples of the IMD 150 can include, but are not limited to, one or any combination of a pacemaker, a pacemaker/defibrillator, a cardiac resynchronization therapy device, a cardiac remodeling control therapy device, or a cardiac monitor. The electronics unit of the IMB 150 can include one or more components that can be enclosed in a hermetically-sealed canister or "can." In an example, the lead 170 can include one or more leads in the cardiovascular system, such as one or more atrial leads, ventricular leads, or one or more intracardiac vasculature (e.g., coronary sinus) leads. Each lead can include one or more electrodes. Other electrodes can be located on the can, or on an insulating header extending from the can, or on or coupled to one or more other portions of the IMB 150, such as for one or any combination of pacing, sensing, resynchronization, neurostimulation, impedance monitoring, cardioversion/defibrillation, etc. In an example, the implantable system 120 can communicate with an ambulatory sensor 180 or a static sensor 190. The ambulatory sensor 180 can be implantable, such as a cardiac impedance sensor, or external, such as a skin-electrode type electrocardiogram (ECG) sensor, a respiratory band sensor, or the like. The static sensor 190 can be included in or coupled to the external monitoring system 140 such as using one or more of various techniques, such as using a wireless telemetry link 130 or a communication cable.

The IMD 150 of the implantable system 120 can include a hardware, software, or firmware state machine circuit 195, such as in the implantable system 120, in the external device 140, or distributed between these or other components. The state machine circuit 195 can use an application-specific integrated circuit (ASIC) constructed to perform one or more particular functions, or a general-purpose circuit programmed to perform such functions. Such a general-purpose circuit can include a microprocessor, a microcontroller, or a programmable logic circuit, or a portion of one or more of these. The state machine circuit 195 can be configured to receive information about one or more physiological characteristics of the subject 110 or of the heart 160, such as from a sensor in the cardiac lead 170 or another ambulatory sensor 180 or the static sensor 190 or other sensors residing in the IMD 150.

The state machine circuit 195 can analyze the one or more physiological sensor signals received from the sensors 170-190 such as to detect a change in heart failure status. The state machine circuit 195 can detect and monitor a time-sequence of physiological events. A discrete sequence of physiological events can indicate a worsening heart failure condition. The state machine circuit 195 of IMB 150 can be coupled to the heart 160, such as via the lead 170, and to the ambulatory sensor 180, such as via a communication link. Examples of the ambulatory sensor 180 can include a heart sounds sensor, an accelerometer, a cardiac impedance sensor, a posture sensor, an acoustic sensor (e.g., microphone), a respiration sensor, a transthoracic impedance sensor, a pressure sensor, an activity sensor, or an external respiratory band sensor such as having piezoelectric or other sensor elements. The state machine circuit 195 can receive information from the external static sensor 190, examples of which can include a scale, a blood analyte sensor, or a respiratory sensory device such as having a mask airflow sensor.

Unlike a myocardial infarction ("MI," sometimes called a "heart attack"), heart failure is a progressive disorder that can develop slowly and almost imperceptibly over time. Signs of worsening heart failure can include fluid congestion and reduced blood flow. These signs not only affect the cardiovascular system, but also the pulmonary, renal, or neural functions. Symptoms of heart failure can be subtle, and can be missed or misdiagnosed as another disorder. But by monitoring over time a series of physiological changes or states, such as for physiological changes that occur in a particular time-sequence and time window, a worsening heart failure condition can be diagnosed. In an example, as discussed in detail below with respect to FIG. 7, a time sequence of states indicative of worsening heart failure can include: (1) elevated filling pressure, followed by (2) fluid accumulation, followed by (3) dyspnea on exertion, followed by (4) dyspnea at rest, such as indicated by signals from the sensors 170-190. To identify these states, in an example, sensor signals can be analyzed, such as to correspondingly determine (1) increasing pulmonary arterial diastolic pressure (PAD) or increased third heart sound, followed by (2) increased weight with decreased thoracic impedance, followed by (3) an increased respiratory rate with a decreased tidal volume during exertion, and followed by (4) an increased respiratory rate with a decreased tidal volume while at rest. In an example, sensor signals can be analyzed, such as to correspondingly determine (1) increasing pulmonary arterial diastolic pressure (PAD) or increased third heart sound, followed by (2) increased weight or decreased thoracic impedance, followed by (3) an increased respiratory rate or a decreased tidal volume during exertion, and followed by (4) an increased respiratory rate or a decreased tidal volume while at rest.

A heart sounds sensor can be implanted, or used externally, such as to measure the heart sounds associated with mechanical vibrations resulting from heart activity and the flow of blood through the heart 160. Heart sounds within a particular cardiac cycle can be referred to by the associated activity. The first heart sound (S1) is associated with the vibrational sound made by the heart during tensing of the mitral valve. The second heart sound (S2) is associated with the beginning of diastole. The third (S3) and the fourth heart sound (S4) are associated with filling pressures of the left ventricle during diastole. A heart sounds sensor can produce an electrical signal that is representative of mechanical activity of a patient's heart. For example, a single heart sounds sensor can provide an indication of a change in regional shortening of the heart wall, an increase in filling pressure, or an increase in heart chamber contractility.

The heart sounds sensor can be used to detect increased filling pressure of the heart. An increase in S3 heart sound intensity can be an indication of elevated filling pressure of the heart and can be indicative of certain pathological conditions of the heart, including heart failure. Systems and methods that can use an index derived from the S3 heart sound to detect heart failure are described in commonly assigned U.S. Pat. No. 7,115,096, entitled "Third Heart Sound Activity Index for Heart Failure Monitoring," which is incorporated herein by reference in its entirety, including its description of detecting and using heart sounds to diagnose heart failure. An increase in filling pressure of the heart can also be detected using a pressure sensor such as a right ventricle chamber pressure sensor, a pulmonary artery pressure sensor, or a left atrial chamber pressure sensor. In some subjects, the increase in filling pressure of the heart can be followed by one or more abnormalities in a subject's electrocardiogram. An example of such abnormality is having an S-wave to T-wave ("ST") interval of the ECG that is elevated, such as by at least a specified amount from an ST interval of a baseline ECG. An ECG can be sensed using surface (e.g., skin contact) ECG electrodes, using implantable electrodes or can be acquired wirelessly. An example of a sensing circuit that can detect an abnormality is a wireless ECG sensing circuit. A wireless ECG is a signal approximating the surface ECG and is acquired without using skin contact electrodes. An example of a wireless ECG is described in the commonly assigned U.S. Pat. No. 7,299,086, entitled "Wireless ECG in Implantable Devices," which is incorporated herein by reference, including its description of a wireless ECG.

Fluid accumulation can be identified through a weight measurement, decreased thoracic impedance, or both. In an example, the static sensor 190 can include an electronic scale, which can be configured to communicate wirelessly to the state machine circuit 195, such as either directly or using the programmer 140. Thoracic impedance can be used to measure an accumulation of fluid within the subject 110, for example fluid around the heart or in or around the lungs. In an example, an implanted impedance sensor can provide a high frequency, low amplitude AC signal, such as to measure the resistance between electrodes implanted within the subject 110. An external transthoracic impedance sensor can be used to similarly measure thoracic impedance using electrodes, such as can be applied to the subject's skin. Because an applied electrical current encounters less resistance in wetter tissue, a decrease in thoracic impedance likely correlates to an accumulation of fluid in the thorax. Systems and methods that can be used for monitoring pulmonary edema or other thoracic fluid status in a subject using thoracic impedance information are described in commonly assigned U.S. Patent Application No. 2009/0069708 entitled "Histogram-Based Thoracic Impedance Monitoring," which is incorporated herein by reference in its entirety, including its description of using thoracic impedance histogram information to compute and provide a lung fluid status indication.

Dyspnea, both during physical exertion and at rest can be predictive of a worsening heart failure condition. In chronic compensated state, a heart failure patient can have an elevated respiration rate. Shortly before a decompensation, the heart failure patient's respiration rate can become more elevated, even at rest. One or more ambulatory or external sensors 180-190 can transmit to the state machine circuit 195 one or more respiration signals that can indicate one or more respiration characteristics of the subject 110. Examples of respiration characteristics can include respiration rate, minute ventilation and tidal volume. The sensors 180-190 can include any variety of sensors, such as an implantable thoracic impedance sensor, external respiratory bands, a respiratory mask flow sensor, or another type of respiration sensor. Examples of techniques that can provide a clinician with a quantifiable respiration metric to monitor a patient's changing heart failure status are described in co-pending, commonly assigned, U.S. patent application Ser. No. 12/787,777, entitled "Respiration Rate Trending for Detecting Early Onset of Worsening Heart Failure," which is incorporated herein by reference, including its description of using a respiration characteristic to monitor heart failure status.

Figure 2:
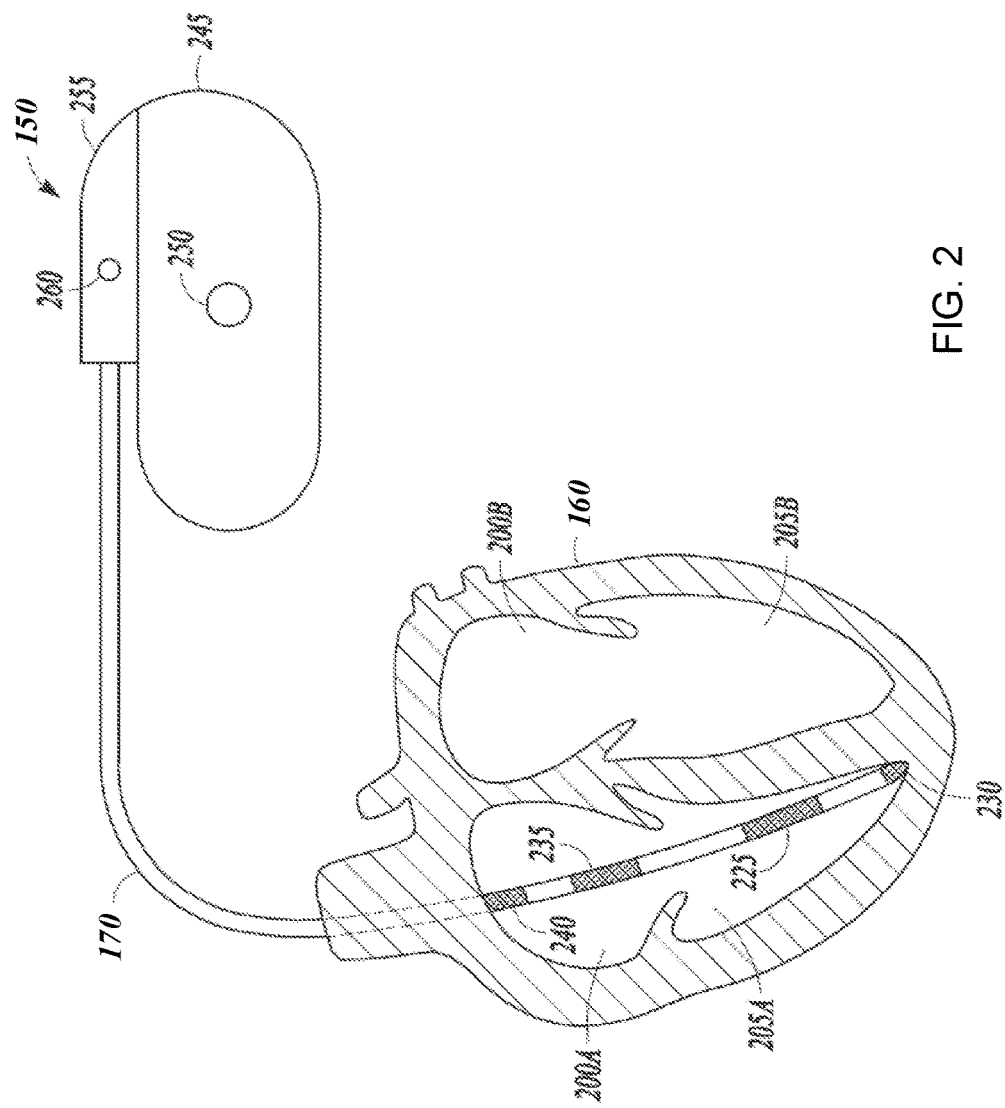
FIG. 2 illustrates an example of an IMB that can be coupled by one or more leads to a desired location such as a heart.

FIG. 2 illustrates an example in which the IMD 150 of FIG. 1 can be coupled by one or more leads 170 to a heart 160. The heart 160 includes a right atrium 200A, a left atrium 200B, a right ventricle 205A, and a left ventricle 205B. The lead 170 can include one or more electrodes (e.g., electrical contacts, such as a coil electrode 225, and a tip electrode 230) that can be sized, shaped, spaced, or otherwise configured to be located in a ventricle 205A of the heart 160, such as for sensing signals or delivering a therapy, or both, such as to or from the ventricle 205A. The lead 170 can additionally or alternatively include one or more electrodes that can be sized, shaped, spaced, or otherwise configured for placement in the right atrium 200A, such as a coil electrode 235 and a coil electrode 240, such as for sensing signals, delivering therapy, or both sensing signals and delivering pacing therapy. The IMD 150 can include a can electrode 250 included at the IMD can 245, or a header electrode 260 included at the IMD header 255.

The IMD 150 can optionally also include one or more additional leads or electrodes, such as for delivering atrial cardioversion, atrial defibrillation, ventricular cardioversion, ventricular defibrillation, or combinations thereof to the heart 160. Optionally, the lead 170 can be implemented as two leads, such as where each lead includes two electrodes. In an example, this arrangement can include a first lead that can include a tip electrode that can be sized, shaped, spaced, or otherwise configured to be located at the apex of the right ventricle 205A and a first ring electrode that can be sized, shaped, spaced, or otherwise configured located in the right ventricle 205A proximal to the tip electrode. In this arrangement, a second lead can include a tip electrode that can be sized, shaped, spaced, or otherwise configured to be located in the right atrium 200A and a ring electrode that can be sized, shaped, spaced, or otherwise configured to be located in the right atrium 200A proximal to the tip electrode.

Optionally, the IMD 150 can include an additional cardiac lead that can include ring electrodes that can be sized, shaped, spaced, or otherwise configured for placement in a coronary vein within and along a wall of the left ventricle 205B. A lead placed in the left ventricle 205B, such as to provide one or more electrodes located in association with the left ventricle 205B. An electrode placed in the right ventricle 205A can be used to optionally provide bi-ventricular resynchronization therapy to the heart 160.

The IMD 150, or the lead 170, can be configured to determine other physiological parameters. For example, the cardiac electrodes of the lead 170 can be used to sense thoracic impedance, such as for determining respiration or thoracic fluid status parameters. Other examples of sensors can include an accelerometer such as for sensing patient activity or posture sensors or heart sounds or the like, a posture sensor, a sense amplifier circuit, such as to determine an electrocardiogram signal, and respiration signal-processing circuitry such as to detect disordered breathing.

Figure 3:
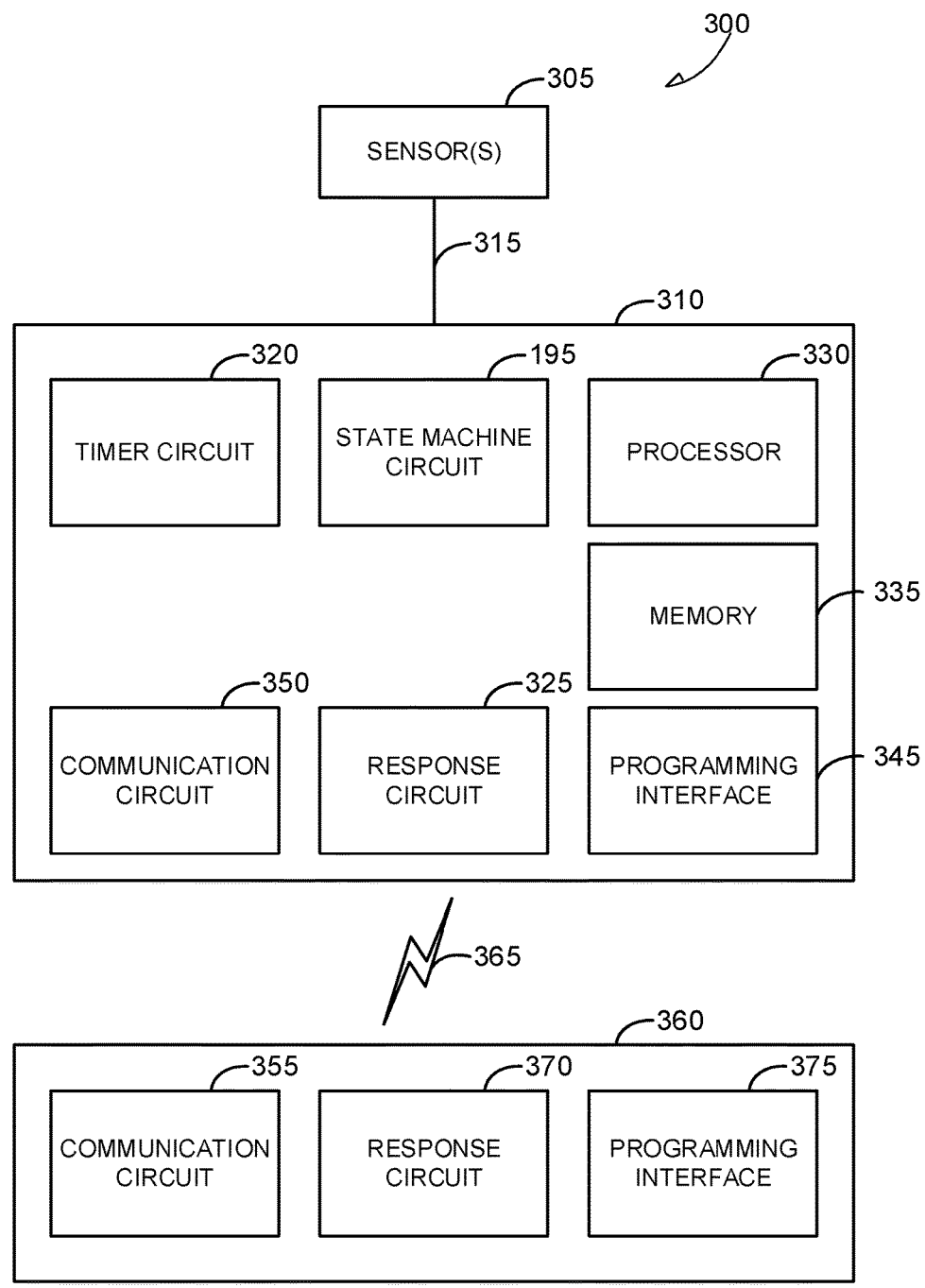
FIG. 3 is an example of a block diagram of portions of an example of a system for detecting a worsening heart failure condition.

FIG. 3 is a block diagram representation of an example of a system 300 that can be configured to detect a changing heart failure condition. The system 300 can include one or more sensors 305 that can be implantable, ambulatory or otherwise external to the subject. The sensors 305 can communicate to a monitoring system 310 such as using a communication link 315, or be included within the monitoring system 310. The monitoring system 310 further can include the state machine circuit 195, such as in communication with a timer circuit 320 and a response circuit 325. The monitoring system 310 can include a processor circuit 330, a memory circuit 345, a programming circuit 345, and a communication circuit 350. The communication circuit 350 can be used for communication between the monitoring system 310 and a remote monitoring device 360, such as using a second communication link 365. The remote monitoring device 360 can include a response circuit 370, a communication circuit 355, and a programming interface 375.

As discussed above, the sensors 305 can monitor physiologic characteristics of the subject 110 and can include any combination of the sensors 170-190, 250, 260. The sensors 305 can provide raw data, such as for further processing, or can include a signal-processing or other circuit that can be capable of processing the raw data into one or more signals, such as physiological sensor signals capable of representing one or more physiologic characteristics or indications. In an example, the physiologic sensor signals can include an S3 heart sound, a pulmonary arterial pressure (PAP), a weight measurement, a thoracic impedance measurement, a respiratory rate, a tidal volume, a physical activity level, or posture information regarding the subject. After gathering (or optionally processing) the data, the sensors 305 can transmit information from the respective physiological signals to the monitoring system 310, such as using the communication link 315. Examples of the communication link 315 can include, but not be limited to, a direct wired connection, an inductive communication link, a radio-frequency (RF) link, a wide area network (WAN) link, or any combination. In an example, the communication link 315 can be connected (e.g., directly) to the state machine circuit 195 within the monitoring system 310, or can be indirectly connected using an intermediate device, such as the device 140.

The state machine circuit 195 can analyze information from the physiological signals from the sensors 305, such as using one or more state machines, such as to detect a worsening heart failure condition. Examples of state machines are described in greater detail below in the description of FIGS. 4-8. An example of a state machine that can be provided by the state machine circuit 195 can include three or more states, with defined transitions to change the current state. Each state can represent a different physiological state of the subject 110, which can be defined in terms of one or more physiological characteristics associated with the measured physiologic signals.

In an example, the state machine can include a first state, a second state and a third state. The first state can correspond to a baseline condition of the subject 110. The second state can correspond to a high fluid state. The third state can correspond to a "dyspnea at rest" state in which the subject 110 experiences dyspnea while at rest. A first transition trigger condition can move the current state from the first state to the second state. In an example, the first transition trigger condition can include at least a specified (e.g., large) increase in weight that is accompanied with at least a specified (e.g., large) decrease in thoracic impedance (e.g., thoracic fluid accumulation). A second transition trigger condition can move the current state from the second state to the third state. In an example, the second transition trigger condition can include a specified (e.g., large) rise in respiratory rate that is accompanied with a specified (e.g., large) decrease in tidal volume that is present without exertion (e.g., without an increase in physical activity). In an example, the last state in the state machine (e.g., the third state in the above example including first, second, and third states) can include an alert state that can be reached after a final transition trigger condition, such as an expiration of a timer. In an example, the alert state can correspond to a hospitalization alert notification state, such as a worsening HF alert notification state, in which an indication of the physiological status of the subject 110, such as a worsening HF alert, can be provided to the subject or a clinician, such as by an audible indication (e.g., a audible alarm), a visual indication (e.g., an illuminated LED), or a notification message (e.g., an email, report, etc.).

In an example, the state machine circuit 195 can be coupled to the timer circuit 320. The timer circuit 320 can create one or more time windows, and can provide the time windows to the state machine circuit 195. For example, the timer circuit 320 can initiate a specified first time window, such as upon the occurrence of the first transition trigger condition, such that if the second transition trigger condition does not occur within the first time window, the current state will return to (or remain in) the first state. The timer circuit 320 can also initiate a specified second time window, such as upon the occurrence of the first transition trigger condition, such that if the state machine does not issue an alert within the second time window, the current state will return to (or remain in) the first state. The timer circuit 320 can be configured to create variable specified time windows, such as a time window value that can be based on an encountered state sequence, a physiological signal value, or a combination of these or other inputs. The timer circuit 320 can be configured to output multiple time windows, each time window being programmable to a different specified value. The timer circuit 320 can be configured to output a "refractory" time window value that can specify a minimum wait time in the current state before the next state transition trigger condition can be recognized.

The state machine circuit 195 can be connected to the response circuit 325. The response circuit 325 can trigger a specified response, such as when the state machine circuit reaches as specified state, such as the final state or the alert state. Examples of responses that can be triggered by the response circuit 325 can include immediately delivering a therapy, communicating an alarm to the subject 110, communicating an alarm to a physician, or any combination.

The device 310 can include a processor circuit 330, a memory circuit 335, a programming interface 345, or a communication circuit 350. The processor 330 can implement all or part of the state machine circuit 195, or can be configured to trigger delivery of therapy, or both. The memory circuit 335 can be used to store data, such as related to the physiologic signals, states and state transitions for communication to a monitoring device, for example the remote monitoring device 360. The memory circuit 335 can also be used during communication with the programming interface 345 such as to store data related to modifying the state machine circuit 195 or the timer circuit 320 operation.

The communication circuit 350 can be used to communicate between the response circuit 325 and a communication circuit 355 of an external monitoring device 360, such as using the communication link 365. The communication circuit 355 can then transmit the specified response to a response circuit 370. For example, the specified response can be an alert to a physician that the subject 110 is experiencing a worsening heart failure condition, a report containing the physiologic data associated with the subject, the trajectory that the patient followed across different states leading up to worsening HF, or any combination. The communication circuits 350 and 355 can be used for communicating between the programming interfaces 345 and 375. The example programming interface 375 can, in an example, allow a physician or other user to modify a specified value of a time window, a parameter associated with a state machine state, a report format, or a state machine transition trigger condition, such as from the remote monitoring device 360, which can be physically separated from the example device 310.

Figure 4:
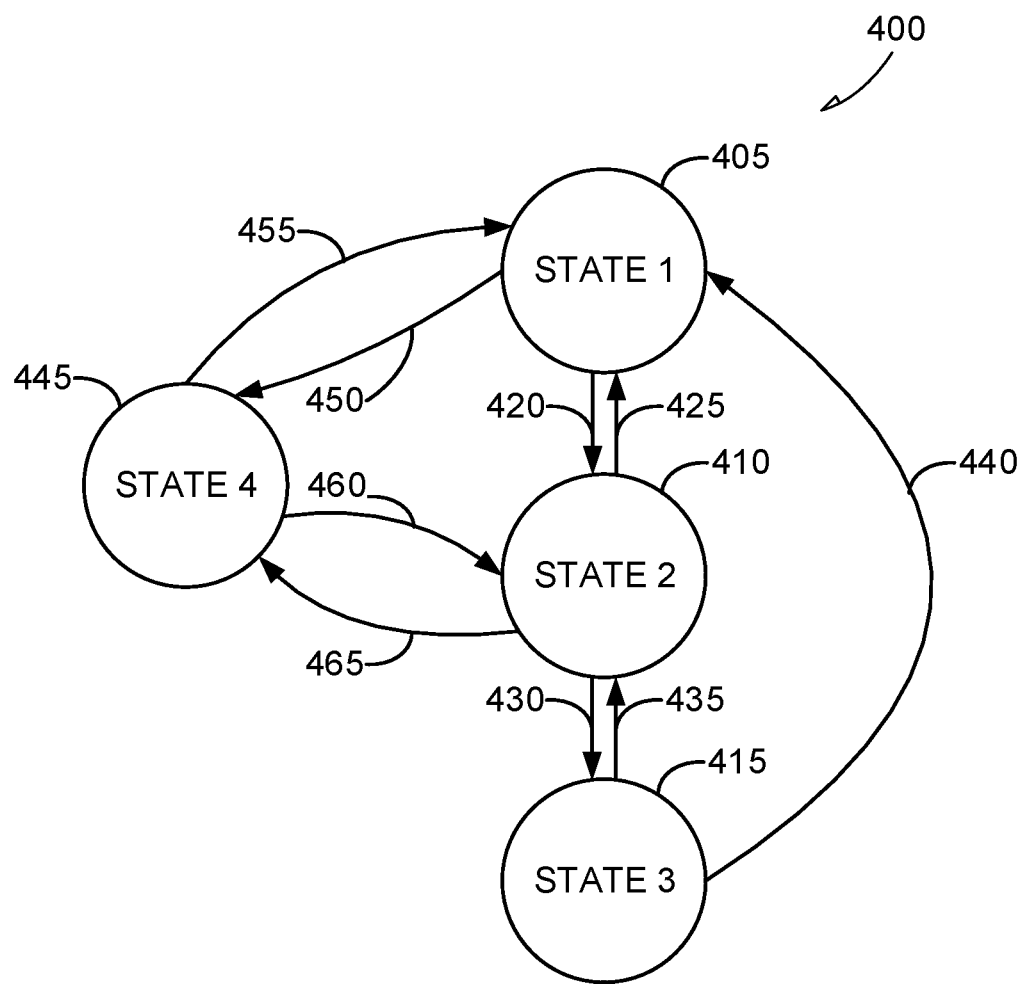
FIG. 4 is an example of a block diagram of an example of a method that can be used for predicting or detecting a worsening heart failure condition.

FIG. 4 is a block diagram representation of an example of a state machine 400 that can be implemented such as using the example state machine circuit 195. The state machine 400 can include a first state 405, a second state 410 and a third state 415. The first state can correspond to a baseline condition of the subject 110. The third state can correspond to an alert state, where the alert state can indicate a worsening heart failure condition or other clinical event. The state machine 400 can include a first forward state transition 420 from the first state 405 to the second state 410, such as in response to a first transition trigger condition, and a first reverse state transition 425 from the second state 410 to the first state 405, such as in response to (1) an expiration of a first timer generated by the timer circuit 320 or (2) the ceasing of the first state transition trigger condition. The state machine 400 can include a second forward state transition 430 from the second state 410 to the third state 415, such as in response to a second transition trigger condition, and a second reverse state transition 435 from the third state 415 to the second state 410, such as in response to (1) an expiration of a second timer generated by the timer circuit 320 or (2) the ceasing of the first state transition trigger condition. The state machine 400 can include a third reverse state transition 440 between the third state 415 and the first state 405, such as in response to the expiration of a third timer generated by the timer circuit 320. In an example, the third timer value can correspond to a maximum time allowable between the first forward state transition and the issuing of an alert before to returning to a beginning state condition, such as a baseline condition for subject 110.

The state machine 400 can further include a fourth state 445 and a third forward state transition 450, such from the first state 405 to the fourth state 445, such as in response to a third transition trigger condition. The state machine 400 can include a fourth reverse state transition trigger condition 455 between the fourth state 445 and the first state 405, such as in response to at least one of (1) the expiration of a fourth timer or (2) ceasing of the third transition trigger condition. The state machine 400 can include a fourth forward state transition 460 from the fourth state 445 to the second state 410, such as in response to a fourth transition trigger condition, and a fifth reverse state transition 465 from the second state 410 and the fourth state 445, such as in response to at least one of (1) the expiration of a fifth timer or (2) ceasing of the fourth transition trigger condition. The ceasing of the first, second, third or fourth transition trigger condition can include a specified change to the transition trigger condition, such as the removal of the transition trigger condition, or a modification of the transition trigger condition alone or in combination with one or more physiological sensor values or other variable inputs.

The timer circuit 320 can configure the expiration value of the first, second, third, fourth, or fifth timer values, such as to specify the same or different values. The timer circuit 320 can further configure one or more of the timer expiration values by computing a variable specified value, such as using as an input one or more physiological sensor values, the number of state transitions, a particular sequence of states that has been encountered, or other variable inputs.

Figure 5:
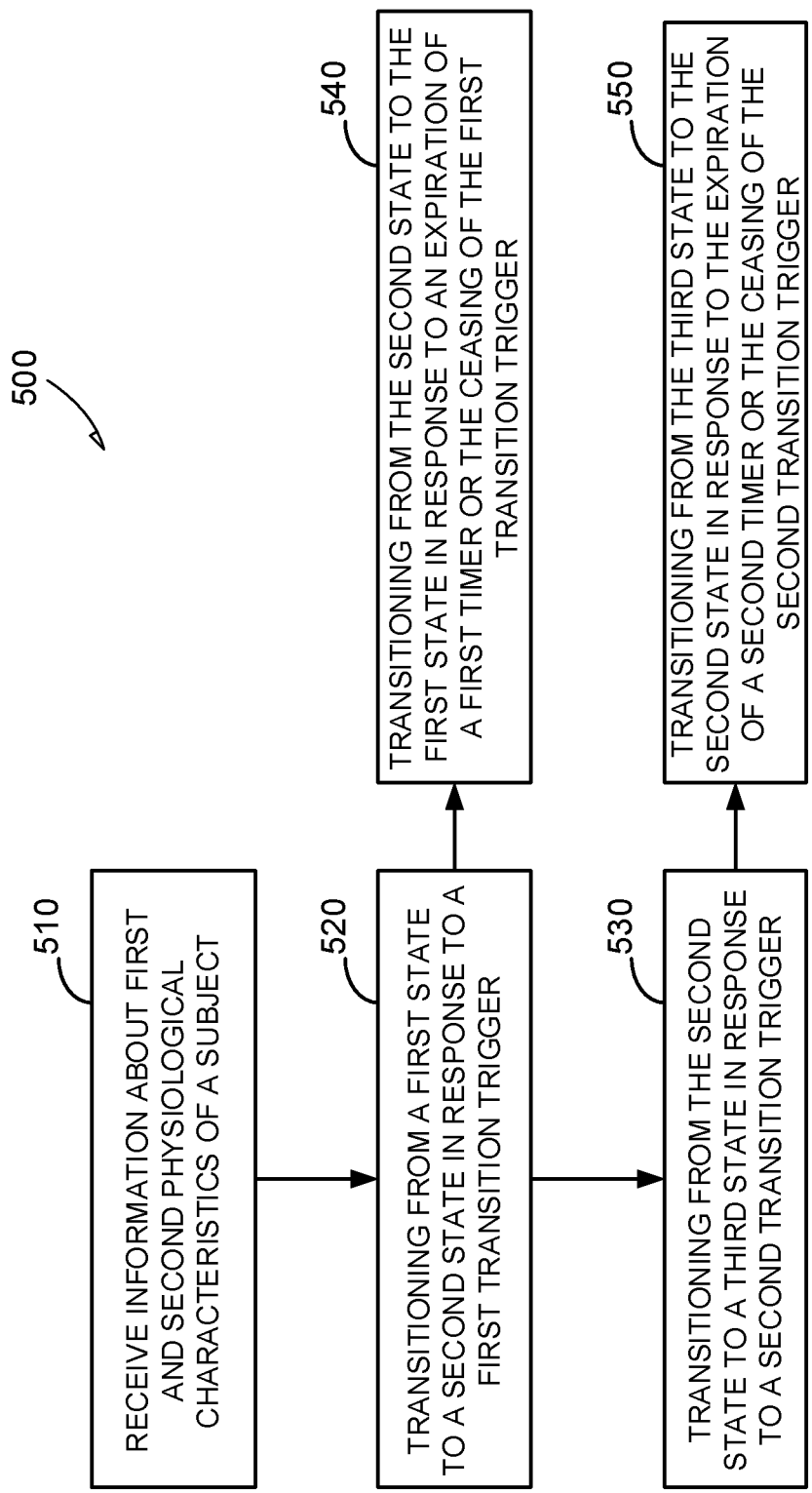
FIG. 5 shows an example of a block diagram of an example of a method that can be used for predicting or detecting a worsening heart failure condition.

FIG. 5 shows a block diagram of an example of a method 500 for detecting a worsening heart failure condition of a subject 110. At 510, a current state, such as of a state machine circuit 195, begins in a first state of the state machine. In an example, in the first state, at least two physiological characteristics of the subject 110 are received. The physiological characteristics can be obtained from one or more physiological signals received from one or more sensors associated with the subject 110. A physiological characteristic (e.g., the third heart sound (S3), or thoracic impedance, etc.) can be obtained from physiological sensor signals of the same sensor or different sensors. The first state can correspond to a baseline condition of the subject 110.

At 520, a first transition trigger condition is recognized by the state machine circuit 195, such as from the physiological characteristics received at 510, causing the state machine to transition the current state from the first state to a second state. In the second state, the state machine waits for one of the following: (1) the ceasing of the first transition trigger condition, (2) the occurrence of a second transition trigger condition, or (3) the expiration of a first timer, where the first timer measures a maximum waiting time for the occurrence of the second transition trigger condition. In an example, the first transition trigger condition can include a rising blood pressure, such as by detecting at least a specified increase in PAP or detecting at least a specified increase in intensity of S3 heart sound. In an example, the first transition trigger condition can include a subject retaining fluid, such as by detecting at least a specified increase in weight or by detecting at least a specified decrease in thoracic impedance. In an example, the first transition trigger condition can include tachypnea, such as at least a specified increase in maximum resting respiration rate.

At 530, the second transition trigger condition is recognized by the state machine circuit 195 and the state machine transitions the current state from the second state to the third state. In the third state, the state machine can wait for one of the following: (1) the expiration of the second trigger, or (2) the expiration of a second timer that corresponds with a maximum waiting time. In an example, the third state can include an alert state. In an example, the third state can include a physiologic state for which an alert can be issued after another condition is met, or a timer expires.

Returning to 520, a transition of the current state from the second state to the first state can be triggered by: (1) an expiring first timer or (2) the ceasing of the first transition trigger condition, thereby proceeding to 540. At 540, the state machine transitions the current state from the second state to the first state, thereby returning to 510.

Returning to 530, the second timer expiring or the second transition trigger condition ceasing can thereby proceed to 550. At 550, the state machine can transition the current state from the third state to the second state, thereby returning to 520. In an example, expiry of a third timer, specifying a maximum time allowed from the occurrence of the first transition trigger condition to the issuing of an alert, can cause a return to 510.

Figure 6:
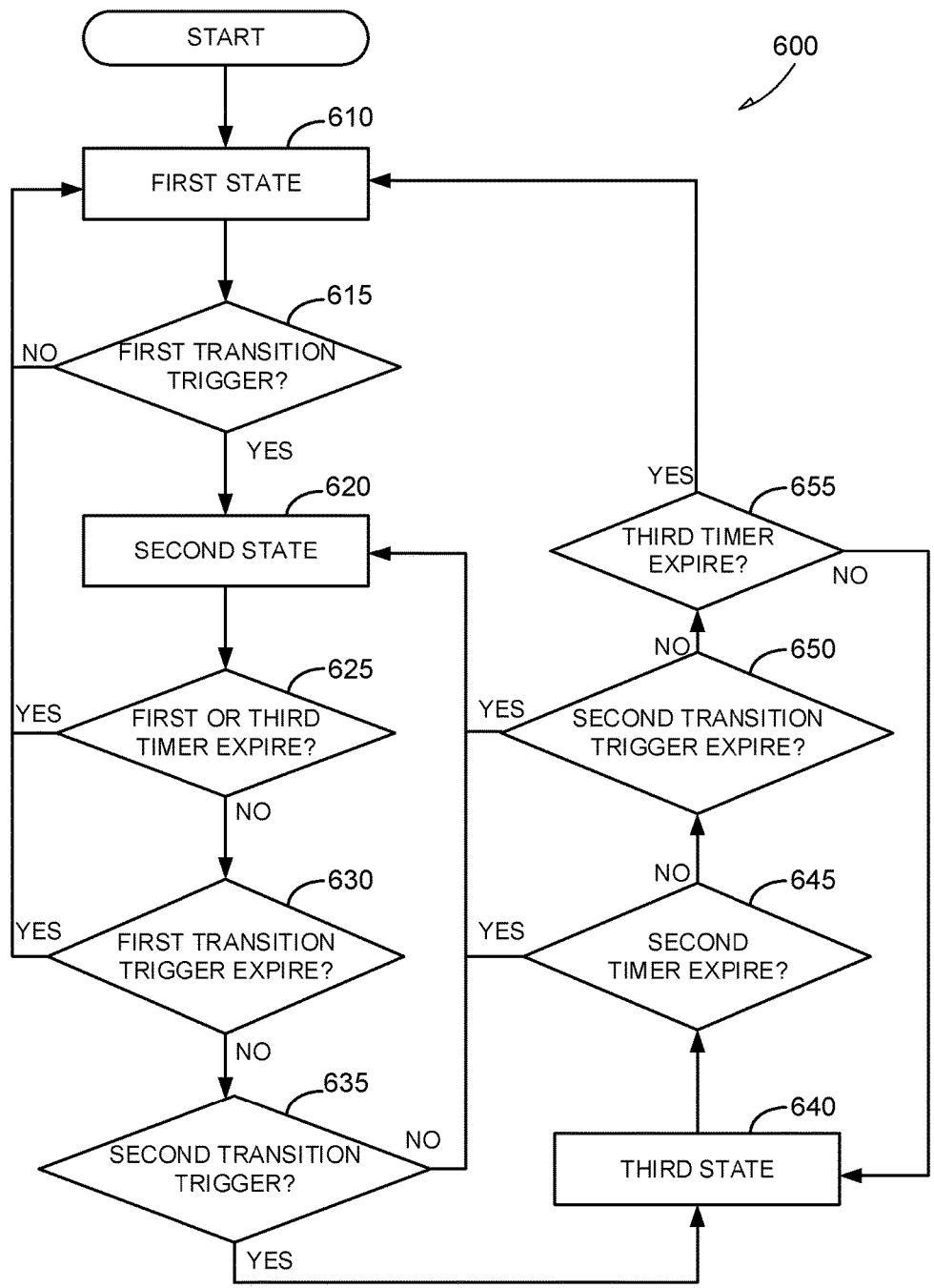
FIG. 6 is an example of a block diagram of an example of a method that can be used for predicting or detecting a worsening heart failure condition.

FIG. 6 is a block diagram of another example of a method to detect a worsening heart failure condition, such as based on a time-sequence of changes in physiological measurements. At 610, a state machine, such as can be implemented using the state machine circuit 195, begins with the current state at a first state. In an example, the state machine can include three states, two transition trigger conditions, and three timers. The first state can represent a baseline condition of a subject, as determined using one or more physiological characteristics. In the first state, the physiological characteristics are monitored for a change representing a worsening heart failure condition. At 615, if the physiological characteristics indicate that a first transition trigger condition has occurred from the monitored physiological characteristics. If the first transition trigger condition has occurred, flow continues to 620. Otherwise, flow returns to 610.

At 620, the state machine has recognized the first physiological change in the time-sequence monitoring scheme. Upon reaching the second state, the first timer and third timer start. The first timer can measure the maximum time allowed for waiting for the second transition trigger condition to occur. The third timer can measure a maximum time between the occurrence of the first transition trigger condition and the occurrence of the second transition trigger condition. At 625, the state machine circuit can determine whether the first or third timers have expired. If so, the state machine can return the current state to the first state and flow moves to 610. Otherwise, flow continues to 630, where the state machine determines whether the first transition trigger condition has ceased. If so, the state machine returns the current state to the first state and flow moves to 610. Otherwise, flow continues to 635, where the state machine determines whether the second transition trigger condition has occurred. If so, flow continues to 640. Otherwise, flow returns to 620 and the state machine remains with the current state being in the second state.

At 640, the current state of the state machine is in the third state, the entry into which can initiate the second timer. In an example, the third state can include an alert state, in which the subject or a caregiver can be notified of the worsening heart failure condition. In an example, the alert can be deferred until the occurrence of a specified event, such as when (1) an alert trigger has occurred, or (2) the expiry of a timer that corresponds to a minimum time that must be spent in the third state before issuing an alert. At 645 and 650, the state machine monitors whether (1) the second timer has expired or (2) the second transition trigger condition has ceased. If either condition is met, flow returns to 620 and the state machine returns the current state to the second state. Otherwise, flow continues to 655 where the third timer can be checked. If the third timer has expired, then the physiological changes did not indicate a worsening heart failure condition and flow returns to 610 and the state machine can return the current state to the first state. Otherwise, flow returns to 640.

Figure 7:
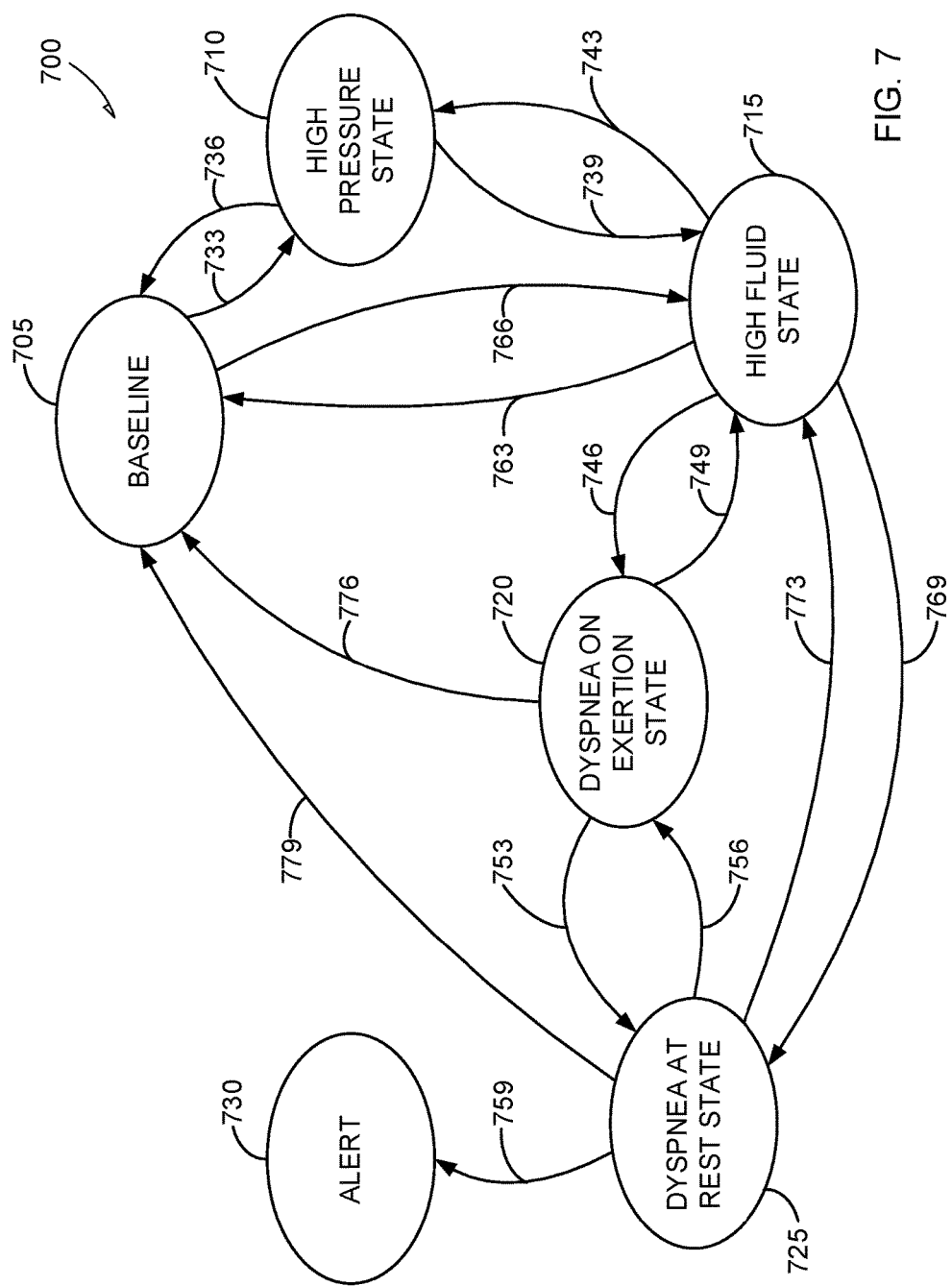
FIG. 7 is an example of a block diagram of an example of a method that can be used for predicting or detecting a worsening heart failure condition.

FIG. 7 shows another example of a state machine to detect a worsening heart failure condition using time-sequence monitoring of physiological characteristics received from sensors associated with a subject. In this example, a state machine 700 can issue a worsening heart failure alert can be issued in response to changes of the subject's physiological characteristics occurring in a specified order within specified time windows. The state machine 700 can include a set of physiological states 705-730 and a set of transitions 733-779 between the states. The states 705-730 can represent the physiological condition of the subject, and the transitions 733-779 can represent the changes to the physiological characteristics of the subject.

In an example, the state machine 700 can include a baseline state 705, a high-pressure state 710, a high-fluid state 715, a dyspnea-on-exertion state 720, a dyspnea-at-rest state 725 and an alert state 730. The state machine 700 can use one or more techniques to ensure the proper time-sequence of state transitions between states, such as by using timers or time windows. For example, a timer or a time window can specify a minimum time that the each state must be active (e.g., a sequence timer), a maximum time to remain in a state before returning to the previous state or the first state (e.g., a state duration timer), or a maximum time allowed to wait for an alert condition to be met from a specified time, such as from the time of the transition out of the baseline state (e.g., an alert timer). The timers can be reset upon a transition or can continue from the previous timer value upon the transition.

The baseline state 705 can correspond to one or more physiologic characteristics that can be specified, for example, by a physician, such as based on a record of the subject's own physiological characteristics, from physiological characteristics of a similar population, through the physician's clinical judgment, or in any combination. In an example, the physiological characteristics can vary over time, such as in response to other physiological characteristics of the subject, to natural variations in the monitored physiological characteristics, or through a physician's clinical judgment.

In an example, the alert state 730 can be reached only when the physiological changes occur in a specified order within certain specified time windows. In an example, physiological changes, such as shown with state transitions 763-769, can modify the current state within the state sequence such as according to changes in the physiological characteristics.

In an example, the state machine 700 can include a time-sequence of physiological changes that can move the subject's state from the baseline state 705 to the high-pressure state 710, to the high-fluid state 715, to the dyspnea-on-exertion state 720, to the dyspnea-at-rest state 725, to the alert state 730. In an example, the state sequence can bypass the high-pressure state 710, and can allow for a transition between the baseline state 705 and the high-fluid state 715 when the physiological changes meet one or more different specified values. In an example, the state machine 700 can bypass the dyspnea-on-exertion state 720 and transition directly to the dyspnea-at-rest state 725 from the high-fluid state 715, corresponding to a different set of physiological characteristic changes.

In an example, the state machine 700 begins with the current state at the baseline state 705. In the baseline state 705, the state machine circuit 195 can monitor physiological signals received from sensors associated with the subject such as to determine changes to physiological characteristics. Specified changes to the physiological characteristics correspond to the state transitions between the states. In an example, the state machine 700 can transition from the baseline state 705 to the high-pressure state 710 when the detected physiological characteristic changes meet the transition trigger condition of the forward state transition 733. In an example, the transition trigger condition for the forward state transition 733 can correspond to at least a specified increase in PAP and at least a specified increase of third heart sound S3. In an example, the transition trigger condition for the forward state transition 733 can correspond to at least a specified increase in PAP or at least a specified increase of third heart sound S3. Upon entry into the high-pressure state 710, the high-pressure state duration, sequence and alert timers can be started. The state machine 700 can remain in the high-pressure state 710 until the condition for one of the state transitions 736-739 are met. In an example, an expiration of the high-pressure state duration timer or the alert timer, or the ceasing of the transition trigger condition can trigger the reverse state transition 736 to the baseline state 705, indicating that the detected physiologic characteristic changes were not symptomatic of a worsening heart failure condition.

The forward state transition 739 from high-pressure state 710 to high-fluid state 715 can be caused by meeting the transition trigger condition, such as at least a specified increase in weight combined with at least a specified decrease in thoracic impedance. In an example, the forward state transition 739 from high-pressure state 710 to high-fluid state 715 can be caused by meeting the transition trigger condition, such as at least a specified increase in weight or at least a specified decrease in thoracic impedance. Upon entry into the high-fluid state 715, the high-fluid state duration and sequence timers can be started. In an example, a forward state transition 766 into the high-fluid state from the baseline state 705 can occur when the trigger condition is met, such as at least a specified (e.g., large) increase in weight with at least a specified (e.g., large) decrease in thoracic impedance. In an example, a forward state transition 766 into the high-fluid state from the baseline state 705 can occur when the trigger condition is met, such as at least a specified (e.g., large) increase in weight or at least a specified (e.g., large) decrease in thoracic impedance. After the forward state transition 766, the high-fluid state duration and sequence and the alert timers can be started.

In an example, the state machine 700 can remain in the high-fluid state 715 until the condition for one of the state transitions 743-746, 763 or 769 are met. In an example, expiring of the high-pressure state duration timer or the ceasing of the transition trigger condition can trigger the reverse state transition 743 to the high pressure-state 710. The expiring of the alert timer can trigger the reverse state transition 763 to the baseline state 705.

The forward state transition 746 from the high fluid state 715 to the dyspnea-on-exertion state 720 can be caused by meeting the transition trigger condition, such as at least a specified increase in respiration rate with at least a specified decrease of tidal volume upon exertion. In an example, the forward state transition 746 from the high fluid state 715 to the dyspnea-on-exertion state 720 can be caused by meeting the transition trigger condition, such as at least a specified increase in respiration rate or at least a specified decrease of tidal volume upon exertion. Upon entry, the dyspnea-on-exertion state duration and sequence timers can be started. The state machine 700 can remain in the dyspnea-on-exertion state 720 until the condition for one of the state transitions 749-753, or 776 are met. In an example, expiring of the dyspnea-on-exertion state duration timer or the ceasing of the forward transition trigger condition can trigger the reverse state transition 749 to the high-fluid state 720. The expiring of the alert timer can trigger the reverse state transition 776 to the baseline state 705.

The forward state transition 753 from the dyspnea-on-exertion state 720 to the dyspnea-at-rest state 725 can be caused by meeting the transition trigger condition, such as at least a specified increase in respiration rate with at least a specified decrease of tidal volume while at rest. In an example, the forward state transition 753 from the dyspnea-on-exertion state 720 to the dyspnea-at-rest state 725 can be caused by meeting the transition trigger condition, such as at least a specified increase in respiration rate or at least a specified decrease of tidal volume while at rest. Upon entry into the dyspnea-at-rest state 725, the dyspnea-at-rest state duration and sequence timers can be started. In an example, a second forward state transition 769 into the dyspnea-at-rest state 725 from the high-fluid state 715 can be triggered by at least a specified (e.g., large) increase in respiration rate with at least a specified decrease of tidal volume while at rest. In an example, a second forward state transition 769 into the dyspnea-at-rest state 725 from the high-fluid state 715 can be triggered by at least a specified (e.g., large) increase in respiration rate or at least a specified decrease of tidal volume while at rest. Following the forward state transition 769, the dyspnea-at-rest state duration and sequence timers can be started The state machine 700 can remain in the dyspnea-at-rest state 725 until the condition for one of the state transitions 756-759, 773, or 779 are met. In an example, the reverse state transition 756 from the dyspnea-at-rest state 725 to the dyspnea-on-exertion state 720 can be triggered by (1) an expiration of the dyspnea-on-exertion state duration timer or (2) the ceasing of the forward transition trigger condition of the forward state transition 753. The reverse state transition 773 from the dyspnea-at-rest state 725 to the high-fluid state 715 can be triggered by (1) an expiration of the dyspnea-on-exertion state duration timer or (2) the ceasing of the forward transition trigger condition of the forward state transition 769. The expiring of the alert timer can trigger the reverse state transition 779 to the baseline state 705.

The alert state 730 can be reached following a forward state transition 759. The forward state transition 759 can be triggered automatically upon reaching the dyspnea-at-rest state 725, following the expiration of a specified timer, or other trigger condition, such as specified by a physician. In an example, an alert can send an indication to the subject to phone or visit a clinician, or send an alert message or report to a physician at a remote office, or both.

Figure 8:
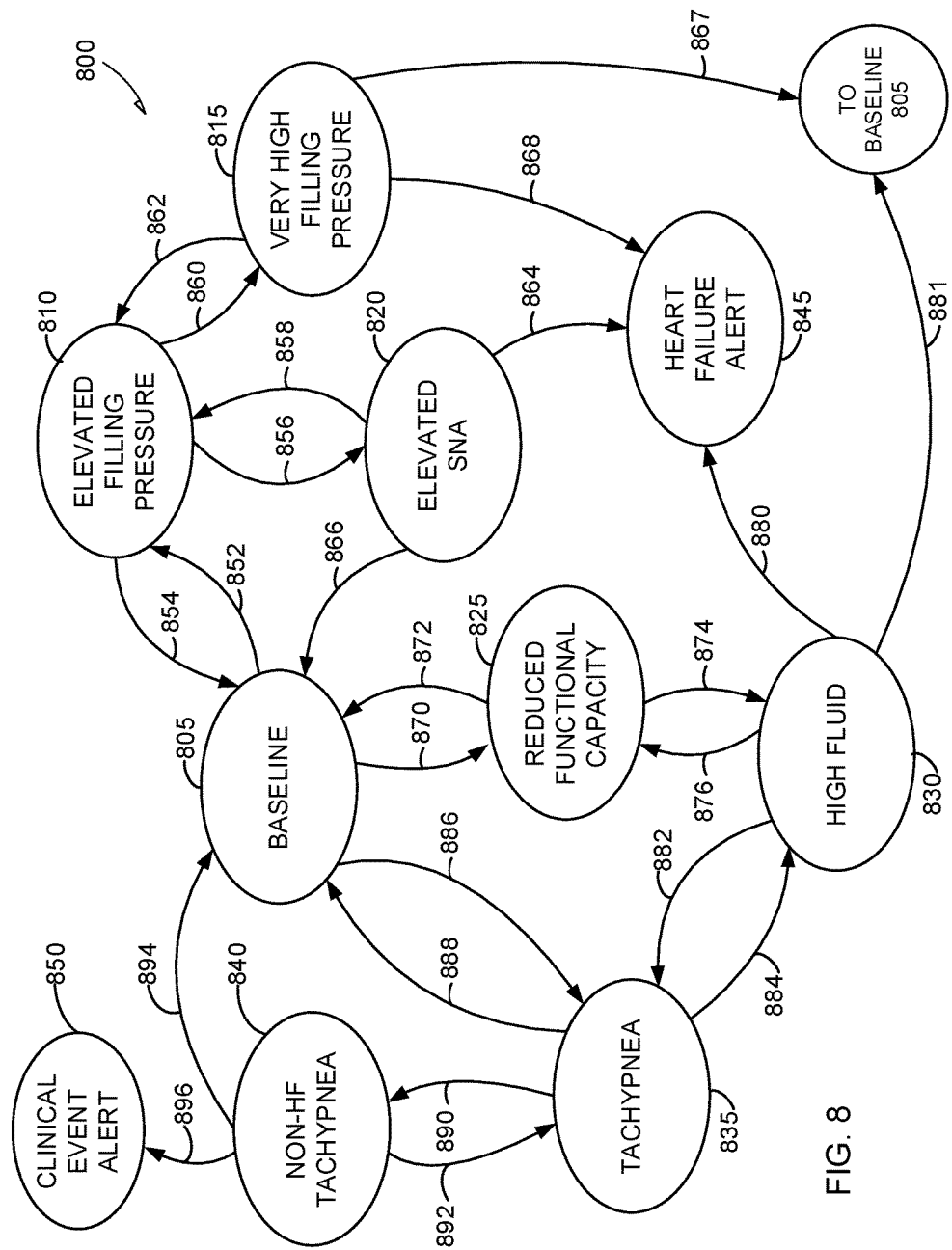
FIG. 8 is an example of a block diagram of an example of a method that can be used for predicting or detecting a worsening heart failure condition.

FIG. 8 is an example of a state machine such as to detect a worsening heart failure condition using time-sequence monitoring of physiological characteristics. In addition to issuing the worsening heart failure alert discussed above with respect to FIG. 7, the state machine 800 can be configured to issue another alert corresponding to a non-heart failure condition. The state machine 800 can include a set of physiological states 805-850 and a set of transitions 852-896 between states. The set of states 805-835 can represent physiological conditions of the subject that can be related to a worsening heart failure condition, and the states 835-840 can represent a non-heart failure clinical event, and the states 845-850 can include alert states. The set of transitions 852-896 can represent the changes to the physiological characteristics of the subject. In an example, the state machine 800 can include a baseline state 805, an elevated-filling-pressure state 810, a very-high-filling-pressure state 815, an elevated-SNA-state 820 (e.g., sympathetic nerve activity (SNA)), a reduced-functional-capacity state 825, a high-fluid state 830, a tachypnea state 835, a non-HF-tachypnea state 840, a heart-failure-alert state 845 (e.g., heart failure (HF)), and a clinical-event alert state 850.

In an example, the state machine 800 can include multiple state sequence paths such as to generate either a heart-failure alert 845 or the clinical-event alert 850. The state machine 800 can begin with the current state at the baseline state 805. The state machine 800 can transition between the baseline state 805 and the elevated-filling-pressure state 810 when the detected physiological characteristic changes meet the transition trigger condition of the forward state transition 852. In this example, the transition trigger condition for the forward state transition 852 can correspond to at least a specified increase of third heart sound S3. Upon entry into the elevated-filling-pressure state 810, the elevated-filling-pressure state duration, sequence and alert timers can be started. The state machine 800 can remain in the elevated-filling-pressure state 810 until the condition for one of the state transitions 854-862 are met. In an example, expiring of the elevated-filling-pressure state duration timer or the alert timer, or the ceasing of the transition trigger condition can trigger the reverse state transition 854 to the baseline state 805, indicating that the detected physiologic characteristic changes were not symptomatic of a worsening heart failure condition.

The forward state transition 860 from the elevated-filling-pressure state 810 to the very-high-filling-pressure state 815 can be caused by meeting the transition trigger condition, such as at least a specified (e.g., large) increase in the third heart sound S3. Upon entry into the very-high-filling pressure state 815, the very-high-filling-pressure state duration and sequence timers can be started. The state machine 700 can remains in the very-high-filling-pressure state 815 until the condition for one of the state transitions 862, 867-868 are met. In an example, an expiring of the very-high-filling-pressure state duration timer or the ceasing of the forward transition trigger condition can trigger reverse state transition 862 to the elevated-filling pressure state 810. The expiring of the alert timer can trigger the reverse state transition 867 to the baseline state 705. The heart-failure alert state 845 can be reached following a forward state transition 868. The forward state transition 868 can be triggered automatically upon reaching the very-high-filling-pressure state 815, following the expiring of a specified timer, or other trigger condition as specified. In an example, an alert can send an indication to the subject to phone or visit a clinician, or can send an alert message or report to a physician at a remote office, or both.

The forward state transition 856 from the elevated-filling-pressure state 810 to the elevated-SNA state 820 can be caused by meeting the transition trigger condition, such as at least a specified increase in the respiratory disturbance index (RDI) or apnea hypopnea index (AHI) or another indicator of an increase in the severity of a sleep apnea condition. Upon entry into the elevated-SNA state, the elevated-SNA state duration and sequence timers can be started. The state machine 800 can remain in the elevated-SNA state 820 until the condition for one of the state transitions 858, 864-866 are met. In an example, an expiring of the elevated-SNA state duration timer or the ceasing of the forward transition trigger condition can trigger reverse state transition 858 to the elevated-filling pressure state 810. The expiring of the alert timer can trigger the reverse state transition 866 to the baseline state 805. The heart failure alert state 845 can be reached after a forward state transition 864. The forward state transition 864 can be triggered automatically upon reaching the elevated-SNA state 820, following the expiring of a specified timer, or other trigger condition as specified.

The state machine 800 can begin with the current state at the baseline state 805 and can transitions between the baseline state 805 and the reduced-functional-capacity state 825 when the detected physiological characteristic changes meet the transition trigger condition of a forward state transition 870. In this example, the transition trigger condition for the forward state transition 870 corresponds to at least a specified increase in the monitored subject's physiologic response to activity (PRA). Upon entry into the reduced-functional-capacity state 825, the reduced-functional-capacity state duration, sequence, and alert timers can be started. The state machine 800 can remain in the reduced-functional-capacity state 825 until the condition for one of the state transitions 872-874 are met. In an example, an expiring of the reduced-functional-capacity state duration timer or the alert timer, or the ceasing of the transition trigger condition can trigger the reverse state transition 872 to the baseline state 805, indicating that the detected physiologic characteristic changes were not symptomatic of a worsening heart failure condition or another clinical event.

The forward state transition 874 from the reduced-functional-capacity state 825 to the high-fluid state 830 can be caused by meeting the transition trigger condition, such as at least a specified decrease of the thoracic impedance. Upon entry into the high-fluid state 830, the high-fluid state duration and sequence timers can be started. The state machine 800 can remain with the current state in the high fluid state 830 until the condition for one of the state transitions 876, 880-882 are met. In an example, an expiring of the high-fluid state duration timer or the ceasing of the forward transition trigger condition can trigger a reverse state transition 876 to the reduced-functional-capacity state 825. The expiring of the alert timer can trigger the reverse state transition 881 to the baseline state 805. The tachypnea state 835 can be reached following a reverse state transition 882, if the state machine 800 entered the high fluid state 830 from the tachypnea state 835 via the state transition 884. The heart-failure alert state 845 can be reached following a forward state transition 880. The forward state transition 880 can be triggered automatically upon reaching the high-fluid state 830, following the expiration of a specified timer, or other trigger condition as specified.

The state machine 800 can begin with the current state at the baseline state 805 and can transition between the baseline state 805 and the tachypnea state 835 when the detected physiological characteristic changes meet the transition trigger condition of forward state transition 886. In an example, the transition trigger condition for a forward state transition 886 corresponds to at least a specified increase of maximum respiratory rate. Upon entry into the tachypnea state 835, the tachypnea state duration, sequence, and alert timers are started. The state machine 800 can remain in the tachypnea state 835 until the condition for one of the state transitions 884, 888-890 are met. In an example, an expiring of the tachypnea state duration timer or the alert timer, or the ceasing of the transition trigger condition can trigger the reverse state transition 888 to the baseline state 805, indicating that the detected physiologic characteristic changes were not symptomatic of a worsening heart failure condition or another clinical event.

The forward state transition 890 from the tachypnea state 835 to the non-tachypnea state 840 can be caused by meeting the transition trigger condition, such as at least a specified increase in the minimum respiratory rate. Upon entry, the non-tachypnea state duration and sequence timers can be started. The state machine 800 can remain in the non-tachypnea state 840 until the condition for one of the state transitions 892-896 are met. In an example, an expiring of the non-tachypnea state duration timer or the ceasing of the forward transition trigger condition can trigger reverse state transition 892 to the tachypnea state 835. The expiring of the alert timer can trigger the reverse state transition 894 to the baseline state 805. The clinical event alert state 850 can be reached following a forward state transition 896. The forward state transition 896 can be triggered automatically upon reaching the non-tachypnea state 840, following the expiring of a specified timer, or other trigger condition as specified.

Although the examples of the state machines of FIGS. 7-8 are discussed as monitoring the development of worsening heart failure conditions, the systems and methods described herein can be used to predict or detect a recovery from a decompensated heart-failure or other clinical event. In an example, discussed in reference to FIG. 4, a block diagram representation of an example of a state machine 400 can be implemented such as using the example state machine circuit 195. The state machine 400 can include a first state 405, a second state 410 and a third state 415 and a fourth state 445. The first state 405 can correspond to a physiological condition representative of an acute decompensated heart-failure or other clinical event of the subject 110. The second state 410 and the fourth state 445 can each correspond to a physiological state that can be indicative of a recovery, such as an improving physiological condition. The third state 415 can correspond to an alert state, where the alert state can indicate an improved physiological condition of the subject 110 such as a return to a baseline state. The forward state transitions 420, 430, 450, 460 and the reverse state transitions 425, 435, 455, 465, in combination with the first, second, third, fourth and fifth timers can correspond to a specified time sequence of events representative of an improving physiological condition.

An example of an ambulatory medical device, such as an implantable medical device (IMD) as discussed above, can include one or more of the features, structures, methods, or combinations thereof described herein. For example, a cardiac monitor or a cardiac stimulator can be implemented to include one or more of the advantageous features or processes described below. It is intended that such a monitor, stimulator, or other ambulatory, implantable or partially implantable device need not include all of the features described herein, but can be implemented to include certain features that provide for unique structures or functionality. Such a device can be implemented to provide a variety of therapeutic or diagnostic functions. It would be desirable for an ambulatory medical device, such as an IMD, to provide monitoring of heart failure in patients who have experienced heart failure or are at risk of developing heart failure.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) can be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A system to detect a condition of worsening heart failure, the system comprising:
   a state machine circuit, configured to receive information about different first and second physiological characteristics of a subject, wherein the state machine comprises:
   a state sequence of at least first, second, and third states, wherein a state represents a physiological status of the subject, and wherein the first state includes a status of post-S2 heart sound energy in a sensed electrical heart sound signal and the third state corresponds to a worsening heart failure event of the subject;
   a first forward state transition from the first state to the second state in response to a first transition trigger, wherein the first transition trigger includes a change in the post-S2 heart sound energy;
   a first reverse state transition from the second state to the first state in response to first of expiration of a first timer and ceasing of the first transition trigger;
   a second forward state transition from the second to the third state in response to a second transition trigger associated with worsening heart failure status of the subject; and
   a second reverse state transition from the third state to the second state in response to first of expiration of a second timer and ceasing of the second transition trigger, and generating an alert indicating worsening heart failure event of the subject otherwise.

2. The system of claim 1, further comprising a third reverse state transition from the third device state to the first device state, wherein the third reverse state transition is in response to expiration of a third timer.

3. The system of claim 1, further comprising a plurality of physiological sensors, wherein the physiological sensors produce respective physiological signals including information about the first and second physiological characteristics.

4. The system of claim 1, further comprising an ambulatory heart sound sensing circuit configured to generate the heart sound signal including the post-S2 heart sound information.

5. The system of claim 4, wherein the first device state comprises a baseline status of post-S2 heart sound energy.

6. The system of claim 1, wherein the first and second transition triggers further include a time sequence parameter, wherein the time sequence parameter corresponds to a minimum time prior to transitioning from the first device state to the second device state or transitioning from the second device state to the third device state.

7. The system of claim 1, including a response circuit coupled to the state machine circuit, wherein the response circuit is operable to provide a specified response following the second forward state transition to the third state.

8. The system of claim 7, wherein the response circuit is configured to generate the alert following the second forward state transition to the third state.

9. The system of claim 7, wherein the response circuit is configured to generate a report following the second forward state transition to the third state.

10. A method of controlling operation of a medical device, the method comprising:
   receiving information about different first and second physiological characteristics of an subject;
   forward transitioning from a first device state to a second device state in response to a first transition trigger, wherein a device state represents a physiological status of the subject, and wherein the first device state includes a status of post-S2 heart sound energy in a sensed electrical heart sound signal and the first transition trigger includes a change in the post-S2 heart sound signal energy;
   transitioning back from the second state to the first state in response to first of expiration of a first timer and ceasing of the first transition trigger;
   forward transitioning from the device second state to a third device state in response to a second transition trigger, wherein the third device state corresponds to a worsening heart failure event of the subject;
   transitioning back from the third state to the second state in response to first of expiration of a second timer and ceasing of the second transition trigger, and generating an alert indicating worsening heart failure event of the subject otherwise.

11. The method of claim 10, further comprising receiving a plurality of physiological signals from respective physiological sensors, wherein the physiological signals include information about the first and second physiological characteristics.

12. The method of claim 10, receiving a heart sound signal from an ambulatory heart sound sensor.

13. The method of claim 10, comprising transitioning from the third device state to the first device state in response to expiration of a third timer.

14. The method of claim 10, wherein the first and second transition triggers further include a time sequence parameter, wherein the time sequence parameter corresponds to a minimum time prior to transitioning from the first device state to the second device state or transitioning from the second device state to the third device state.

15. The method of claim 10, wherein the first device state comprises a baseline status of post-S2 heart sound energy.

16. The method of claim 10, wherein the third device state corresponds to a clinical event of a subject.

17. The method of claim 16, further comprising communicating a specified response after transitioning from the second device state to the third device state.

18. The method of claim 17, wherein the specified response includes the alert and a report.

\* \* \* \* \*